US007400752B2

(12) United States Patent  
Zacharias

(10) Patent No.: US 7,400,752 B2
(45) Date of Patent: Jul. 15, 2008

(54) VIDEO OVERLAY SYSTEM FOR SURGICAL APPARATUS

(75) Inventor: Jaime Zacharias, Santiago (CL)

(73) Assignee: Alcon Manufacturing, Ltd., Fort Worth, TX (US)

( * ) Notice: Subject to any disclaimer, the term of this patent is extended or adjusted under 35 U.S.C. 154(b) by 1787 days.

(21) Appl. No.: 10/078,515

(22) Filed: Feb. 21, 2002

(65) Prior Publication Data

US 2003/0159141 A1    Aug. 21, 2003

(51) Int. Cl.
G06K 9/00    (2006.01)
(52) U.S. Cl. .................. 382/128; 348/207.1; 725/37
(58) Field of Classification Search ............ 382/128, 382/129, 130, 131, 132, 133, 134; 348/207.1, 348/E5.093, E5.099; 600/1, 101, 102, 111, 600/126, 407, 426, 427, 478; 602/903; 623/1.11, 623/2.11, 6.12, 22.12; 128/852, 887; 725/37, 725/81

See application file for complete search history.

(56) References Cited

U.S. PATENT DOCUMENTS 5,825,982 A * 10/1998 Wright et al. .............. 700/259
6,602,185 B1 * 8/2003 Uchikubo ................... 600/118
6,751,473 B1 * 6/2004 Goyal et al. ............. 455/556.1

* cited by examiner

Primary Examiner—Abolfazl Tabatabai
(74) Attorney, Agent, or Firm—Jeffrey S. Schira

(57) ABSTRACT

An improved computer based surgical video overlay system that allows relevant surgical data from a surgical apparatus to be combined as a graphic image with the video image of a surgical procedure in which the data from the surgical apparatus is sent wireless to the video overlay console. Elimination of the data cable between the surgical apparatus and the video overlay console is advantageous in an operating room environment. The same computer based surgical video overlay system runs computer program that occupies a user interface to allows definition of operation modes, input of relevant data, selection of data overlay graphic screen templates and various methods for customization. A time coded-data file is created and stored including all the relevant parameters of a surgical procedure. This file contains the same time-code included in the graphic image overlaid in the surgical video signal. An precise match can be performed between the recorded data on file and the surgical video recording. An audio pre-amplifier section is provided to include surgical apparatus meaningful sounds produced during surgery. The alternative embodiment considers the use of an embedded computer within the video overlay console making the system capable of standalone operation providing a user interface and data input/output capabilities.

17 Claims, 7 Drawing Sheets

VIDEO OVERLAY SYSTEM FOR SURGICAL APPARATUS

BACKGROUND

1. Field of the Invention

The present invention generally relates to devices used for superposing computer generated graphic information over portions of another video image and more particularly is related to a device for producing an output video signal of a surgical procedure where portions of the video image are replaced by computer generated graphic information in digital video format derived from a data signal containing meaningful operational parameters from a surgical apparatus.

2. Description of Prior Art

Typically, a surgical procedure such as a cataract surgery may be video-recorded for documentation, research, learning or teaching. As a mode of example, during cataract surgery, a video camera will be located in the surgical microscope receiving an image through a beam splitter that is similar to the surgeons view of the surgical area. Current techniques for cataract removal consider the use of ultrasonic energy in various modalities, vacuum at variable levels, irrigation of fluid and other variables that affect the course of the surgical procedure according to the surgical technique. Ultrasonic energy delivery can be made in a continuous way, or can be pulsed in different modulation schemes according to surgeon preferences. Irrigation pressure is determined by the height of a fluid bottle or gas positive pressure. Fluid aspiration rate can be set in a wide range of values. Vacuum in the aspiration line is situation dependent varying according to preset vacuum limit, occlusion state of the ultrasonic probe, aspiration rate, type of ultrasonic needle being used among others.

There are meaningful parameters that the surgeon can wish to stamp in real time together with the video signal corresponding to the surgical events as viewed through the video-camera. This is specially important when the surgical case is being video-recorded and allows direct correlation between the recorded video image of the surgery and the surgical equipment settings and variables present at each precise moment of the surgery. Some meaningful data desirable to record with the surgery are machine characteristics, aspiration line vacuum, aspiration rate, ultrasonic power, ultrasonic modulation settings, tip occlusion, aspiration line venting, cassette and tubing type among others. Some of these data will remain constant during the whole surgical case such as the equipment model, and others will change because different settings are selected along the case by the operator or because they are situation dependent, such as aspiration line vacuum.

Dedicated "data-over-video" systems for surgical apparatus, from here referred to as "video overlay systems" have been developed to perform the action of superposing an image representing surgical equipment generated parameters to the video signal of the video-captured surgical procedure. As a mode of example, the "Alcon Legacy 20000 Phacoemulsification Console" and the "Allergan Sovereign Phacoemulsification Console" are state-of-the-art ultrasonic based cataract removal surgical apparatus. Video overlay systems can be obtained that are configured for the each surgical apparatus. Operation of these video overlay systems requires a physical connection between the phacoemulsification apparatus and the video overlay system comprised by an electric cable that transmits data in a RS-232 serial protocol to create the graphic representation of the data at the video overlay system level. The video signal from a surgical video-camera mounted on the surgical microscope is input to the overlay system. The processed video output signal that exits the overlay system contains the video image from the video-camera as a background image with overlying portions that display a graphic representation of the data received from the surgical apparatus data output.

It is a main limitation of current video overlay systems for ophthalmic surgical apparatus the need to physically connect an electric data cable between the surgical equipment and the video overlay system to carry the data to create a graphic representation for superposition. It is of common occurrence that this cable runs loose between the surgical apparatus console located near the surgical field and the video overlay console which is usually located near a video recorder to which it is electrically connected through a video connecting cable. The video overlay system is also electrically connected to the video-camera. The surgical video-camera is attached to an operating microscope and is usually stationary. The video recording system and video-monitor used to store and monitor the video images respectively are also usually stationary. On the contrary, surgical apparatus such as a phacoemulsification apparatus are usually mobile and enter and exit different operating rooms according to the scheduled cases. The need to hook up a data cable every time the surgical apparatus is to be used distracts operating room personal from performing other helpful tasks and may discourage the use of the overlay system. More important, the presence of this cable usually flying around in a busy operating room can lead to damage of valuable equipment and even injuries to persons if engaged or pulled by accident.

Another limitation of current video overlay systems for ophthalmic surgical apparatus is the inability to allow a user to customize the set of data he wishes to be included in the video signal to be recorded. Although some limited physician information such as doctor's name can be included in some systems, these data are entered at the surgical apparatus level in a cumbersome fashion. There is no provision in current video overlay systems to include individual surgeon-relevant information such as patient's Id, diagnosis, technique, facility Id and logo at a video overlay system level.

Another limitation of current video overlay systems for ophthalmic surgical apparatus is their inability to produce a time-code that is recorded in a graphic representation over the surgical video in correspondence with a matching time-coded digital file of the meaningful surgical parameters.

Another limitation of current video overlay systems for ophthalmic surgical apparatus is their inability to modify the video overlay system display mode under user commands to change between data graphics overlay mode, video-only mode, or other user configurable overlay templates such as facility Id and logo, according to surgical conditions and user requirements.

Another limitation of current video overlay systems for ophthalmic surgical apparatus is the absence of a feedback signal, preferably visual, at a video overlay console level regarding the proper status of the input data and video signals to help in the installation and debugging of the system prior to operation.

Still another limitation of current video overlay systems for ophthalmic surgical apparatus is that they do not provide a corresponding audio signal carrying surgical apparatus and operating room sounds to be simultaneously recorded with the video signal through a video-recorder audio input.

3. Objects and Advantages

Accordingly, several objects and advantages of my invention are:

To provide a surgical apparatus video overlay system that receives the data signal from the surgical apparatus used to create the graphic overlay by wireless means eliminating the need of a data cable.

To provide a surgical apparatus video overlay system that allows the user to easily include selected sets of data according to personal preferences such as patient's Id, diagnosis, technique, facility name, logo and comments at a video overlay console level. For this purpose different templates can be selected from a menu including manufacturer and eventually user created graphic templates to produce the overlay graphic image.

To provide a surgical apparatus video overlay system capable of producing a time-coded output video signal as well as a matching time-coded digital file of the meaningful surgical parameters. The digital file can be stored in digital media for later retrieval and analysis eventually in correspondence with the surgical case video recording.

To provide a surgical apparatus video overlay system that allows modification of the video overlay system display mode under user commands making possible to change between data graphics overlay mode, video-only mode, or other user configurable overlay templates such as facility Id and logo, according to surgical conditions and user requirements. The change between the different video overlay system operating modes can be instructed at an overlay system user interface level, at a surgical apparatus user interface level including the foot-pedal, or by pre-programming actions that respond to surgical situations such as entering video-only mode after a time-out period of surgical apparatus inactivity.

To provide a surgical apparatus video overlay system that informs the user with specific feedback signals that reflect the proper status of the video and data input signals required by the unit to operate for expedite setup and debugging.

To provide a surgical apparatus video overlay system that includes an audio processor capable of producing an audio output signal related to the surgical apparatus actions and events and operating room sounds, that can be recorded on the audio track of the video recorder simultaneously with the video signal.

Further objects and advantages of my invention will become apparent from consideration of the drawings and ensuing description.

DRAWING FIGURES

The advantages and features of the present invention will be better understood by the following description when considered in conjunction with the accompanying drawings in which.

Figure 1:
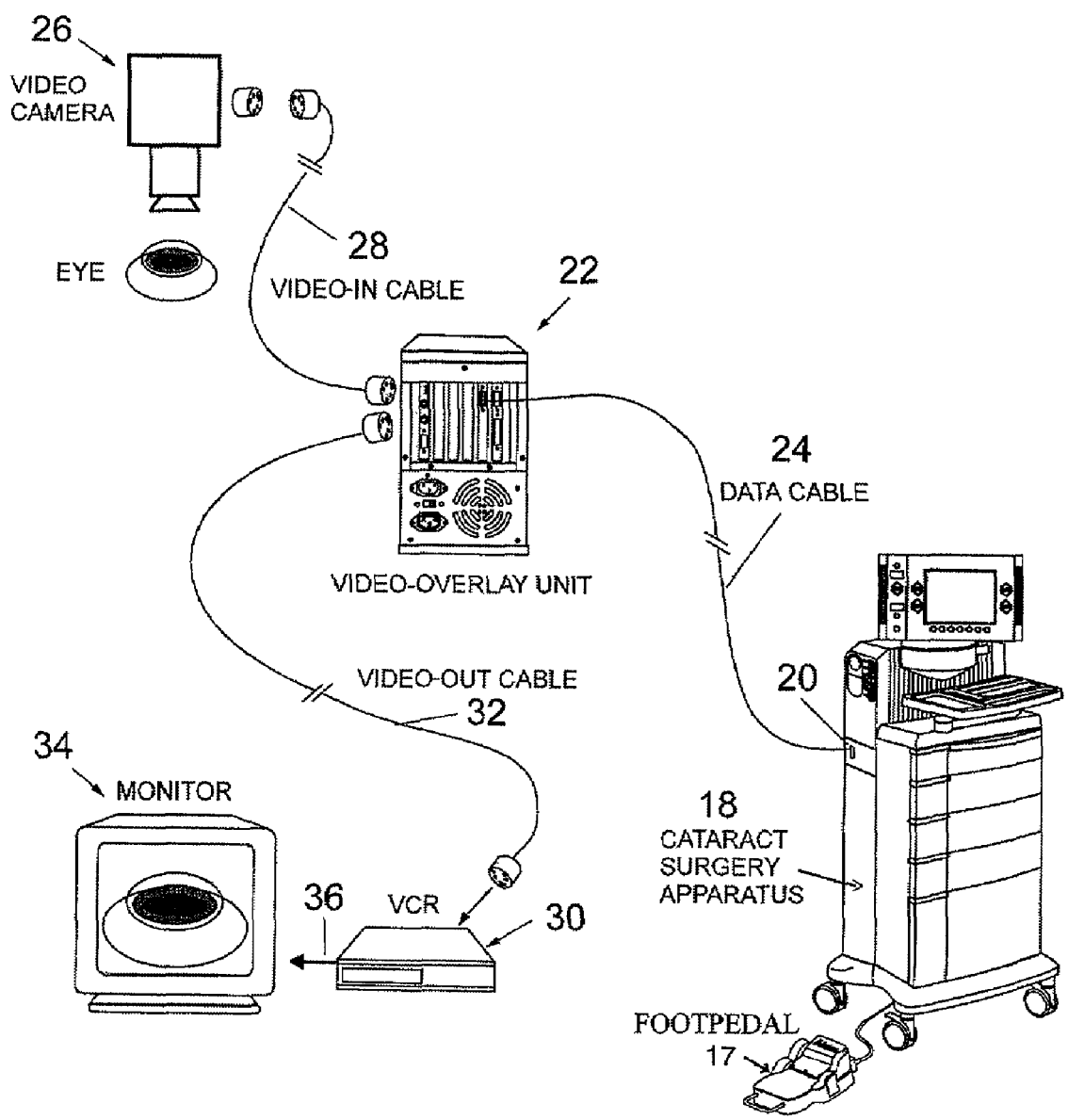
FIG. 1 (PRIOR ART) is a schematic diagram of the video overlay system and the required physical signal connections with a surgical apparatus, a video-camera and a video recorder.

LIST OF REFERENCE NUMERALS 10 wireless video overlay system
17 surgical apparatus foot-pedal 60 file input/output device
18 ophthalmic surgical equipment 62 user control panel
19 surgical apparatus user interface 70 Y/C video signal input port
20 data output port 72 composite video signal input port
22 video overlay console 78 digital-RGB video signal input port
24 data cable 82 video overlay circuit sub-system
26 surgical video-camera 84 composite video output port
28 video input cable 90 Y/C video output port
28a Y/C input video cable 92 audio preamplifier
28b composite input video cable 94 audio output port
30 video-recorder 96 serial data port
32 output video cable 100 embedded computer
32a Y/C output video cable 102 embedded computer data port
32b composite output video cable 104 embedded computer VGA output
34 video monitor 108 embedded computer audio generator
36 monitor video signal cable 110 signal detector circuit
40 wireless data transmitter module 112 signal status indicator panel
42 wireless data receiver module 120 overlay circuit video input signal
43 data input cable connector 121 overlay digital-RGB input signal
44 microphone 122 scan converter/genlock circuit
48 audio output cable 123 genlocked digital-RGB signal
50 VGA cable 124 video mixer circuit
51 serial data port 126 keyer circuit
52 serial data link 128 digital-RGB overlay video signal
56 computer

SUMMARY

In accordance with the present invention a video overlay system for a surgical apparatus comprises a computer operated video overlay console receiving a data stream sent by wireless means by a data transmitter from a surgical apparatus. The video overlay console also receiving a video signal from a surgical video-camera, and producing an output video signal with an overlaid graphic representation of the received data and also producing a computer file with the received data for storage in digital media.

Figure 2:
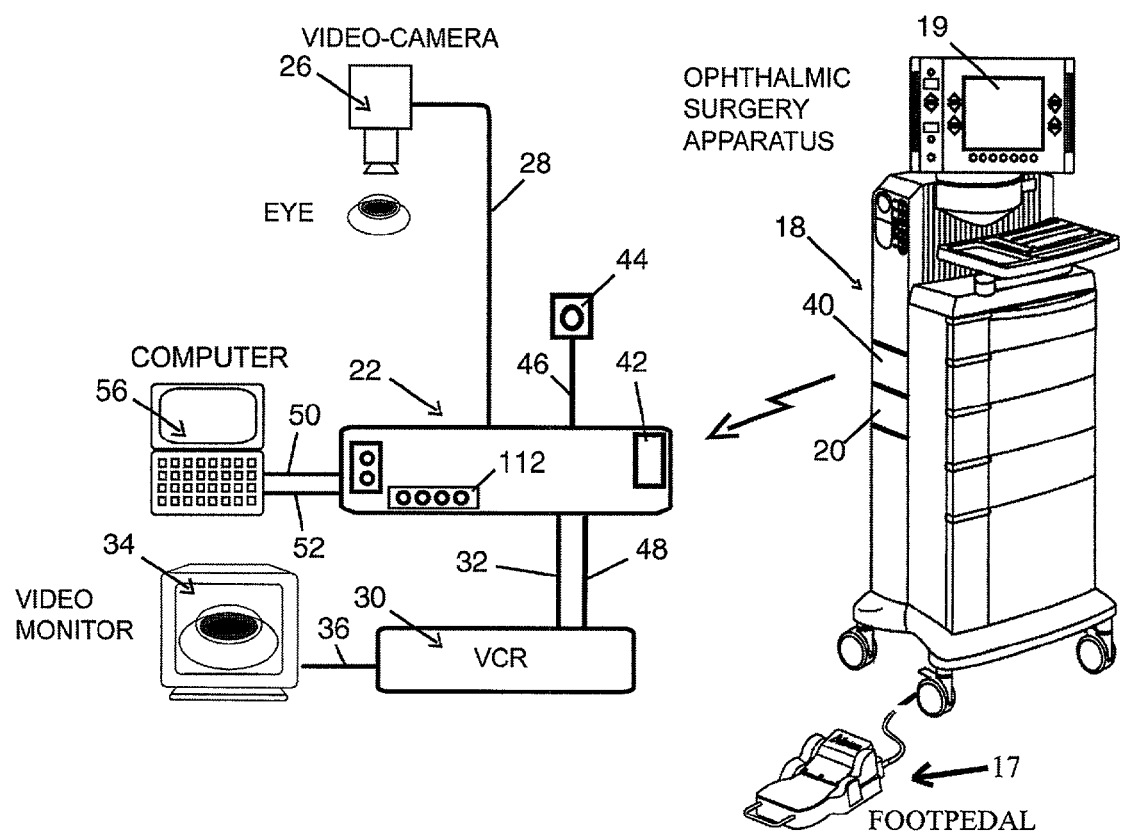
FIG. 2 is a schematic diagram of the video overlay system of the present invention and the required signal connections with a video-camera, a video-recorder and a computer. A radio-frequency data transmitter module within a surgical apparatus is part of the video overlay system.
Figure 3A:
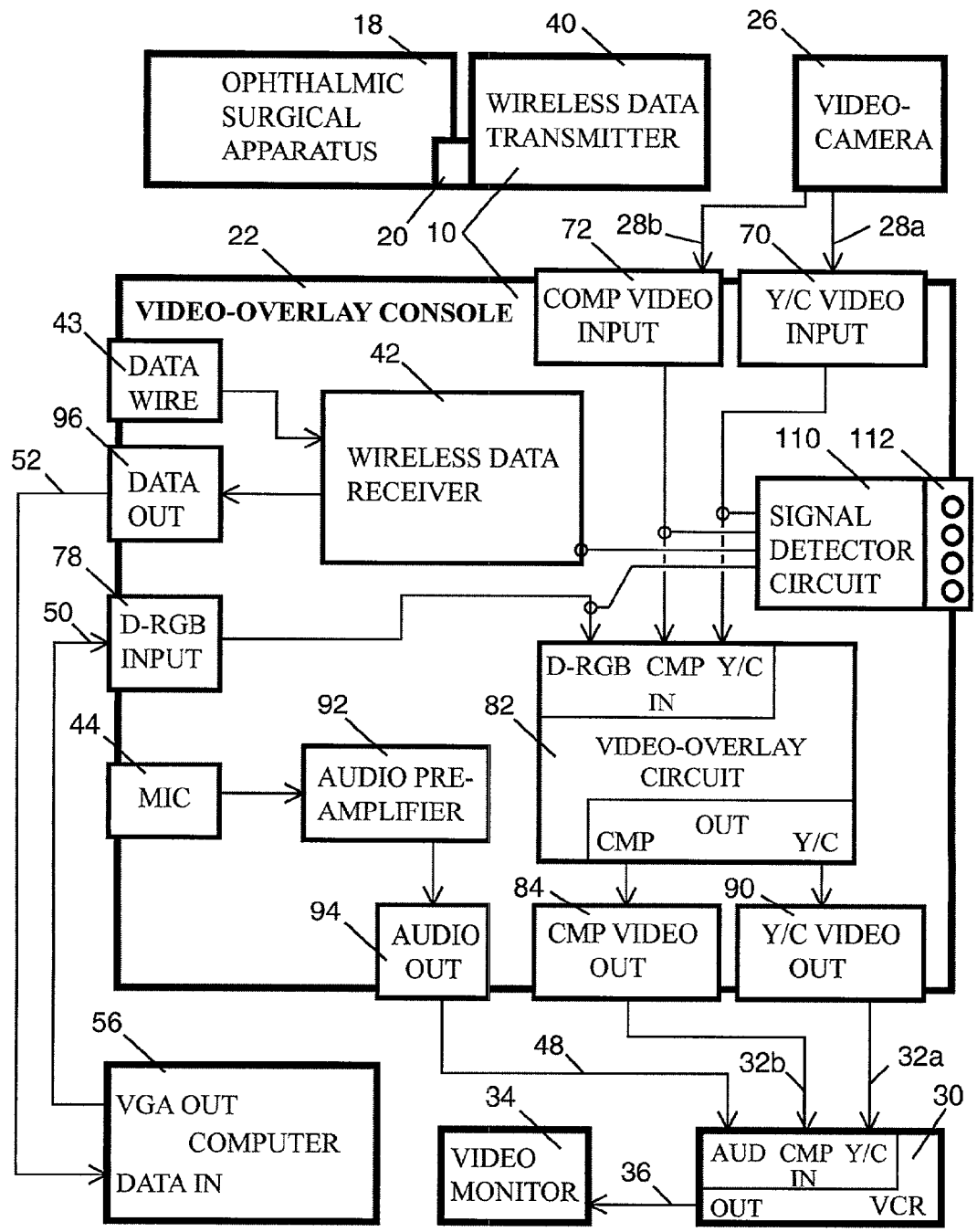
FIG. 3a is a block diagram of the components of the main embodiment of the video overlay system of the present invention.
Figure 3B:
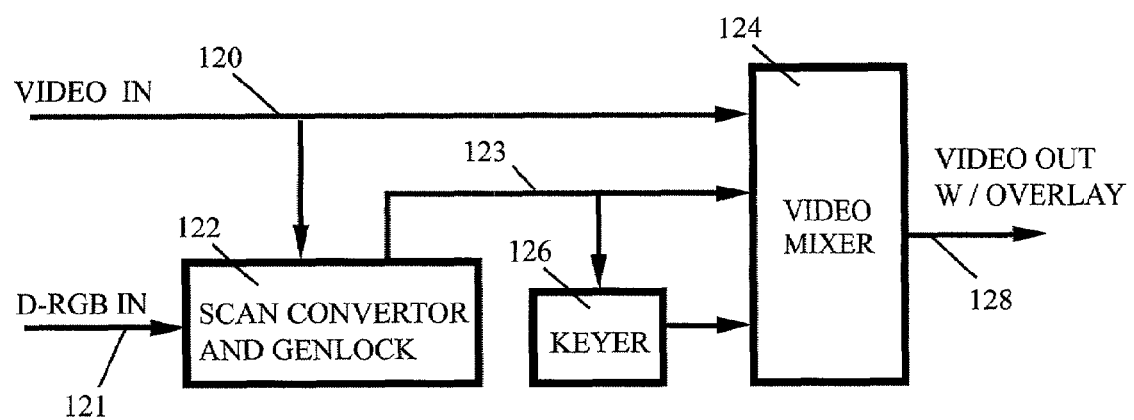
FIG. 3b is a block diagram of the components of the video overlay circuit sub-system of the present invention.

Description—FIGS. 2, 3A and 3B

FIG. 2. shows an overall view and FIG. 3a. shows a detailed block diagram of a video overlay system 10 of the present invention and its interconnections. The video overlay system 10 is composed of a video overlay console 22, an interconnected computer 56 and a physically detached wireless data transmitter module 40 placed in close proximity to a surgical apparatus 18. Surgical apparatus 18 has a foot-pedal 17, a user interface 19 and a data output port 20 that electrically connects to wireless data transmitter module 40. A surgical video-camera 26 provides a video output signal connected to video overlay console 22 through video input cable 28. This connection can be made either by a video cable 28a to a Y/C video input 70 or by a video cable 28b to a composite video input 72 selecting the best signal available. A wireless data receiver module 42 is part of video overlay console 22. Wireless data receiver module 42 serial output is connected to a serial data port 96. Data wire connector 43 also internally connects to serial data port and provides an alternative input data port. A cable 52 connects serial data port 96 to a serial port 53 of computer 56. Computer 56 has a VGA output port 53 that is connected to a digital-RGB video signal input port 78 through a VGA cable 50. Digital-RGB video input signal port 78 internally connects to a video overlay circuit sub-system 82 (FIG. 3B). Video overlay circuit sub-system 82 also alternatively receives the video signals from composite video input 72 or Y/C video input 70. Video overlay circuit 82 provides a composite video output port 84 and a Y/C video output port 90. Composite video output port 84 is connected to a composite video input of a video-recorder 30 through composite output video cable 32b. Alternatively, Y/C video output port 90 is connected to an Y/C video input of video-recorder 30 through an Y/C output video cable 32a. A signal detector circuit 110 is internally connected to the video 70, 72, data 96 and digital-RGB 78 signals and provides a signal status indicator panel 112 usually composed of individual LEDs. A microphone 44 is connected to an audio pre-amplifier 92. The output of pre-amplifier 92 is connected to an audio input connector of video-recorder 30 through an audio output cable 48. The video output connector of video-recorder 30 is connected to the video input connector of a video monitor 34 through a monitor video signal cable 36.

Operation—FIGS. 2, 3A and 3B

A surgical apparatus 18 for performing cataract surgery such as an Alcon Legacy 20.000 phacoemulsification unit, Alcon, USA, provides during operation a serial data stream through serial data port 20 that is input to data transmitter module 40 (such as Model X09-009WM, 9Xstream Wireless OEM Module, MaxStream Inc, USA). The serial data stream is composed of approximately 30 characters followed by line feed and carriage return characters. Characters are encoded in ASCII format at 9600 baud and updated every 100 milliseconds. The characters contained in the data stream represent operating parameters of surgical apparatus 18 as well as meaningful information related to the particular surgical conditions during surgery. Contained in the serial data signal are foot-pedal 17 positions, surgical apparatus 18 aspiration line vacuum, aspiration rate, ultrasonic power, among other relevant data. The serial data stream can contain command characters input at surgical apparatus 18 user interface 19 that modify video overlay console 22 operational modes.

The serial stream is radio-transmitted by data transmitter module 40 in the form of a 900 MHz radio-frequency. Video overlay console 22 contains a matching wireless data receiver 42 (such as Model X09-009WM, 9Xstream Wireless OEM Module, MaxStream Inc, USA.) that receives and decodes the radiated serial data stream sent by wireless data transmitter module 40 providing an identical serial data stream at serial data port 96 as the one present at surgical instrument 18 serial port 20. Multiple wireless transmitter modules 40 installed on different surgical apparatus 18 can be easily set to match the channels of any particular video overlay console 22 wireless receiver module 42 allowing exchange for inter-operability of transmitters and receivers.

Video-camera 26 simultaneously captures the surgical procedure images and provides a video signal in the form of composite video or in the form of Y/C video depending on the video-camera 26 model. Y/C video separates the chrominance and the luminance signals thus providing improved bandwidth over composite video (that multiplexes both signals in a single conductor). Thus the Y/C video signal should be preferred when available. Composite video input port 72 receives a composite video signal from video-camera 26 through composite video cable 28b. Alternatively, Y/C video input port 70 receives an Y/C video signal from video-camera 26 through composite video cable 28a. The composite video signal and Y/C video signal are connected to the corresponding inputs at video overlay circuit sub-system 82 (such as Real-time Genlock, Overlay and Computer to Video Conversion Device. Coriogen Eclipse, Vine Micros Ltd, UK) detailed in FIG. 3B. The video-camera 26 video signal is used as the running video background image for video output 128. Simultaneously, serial data port 96 provides the wireless-received serial data stream to computer 56 serial data port 51 through serial cable 52.

A Pascal language written computer program running on computer 56 reads and separates each incoming serial data stream into the original parameters according to the surgical apparatus 18 encoding scheme. Computer 56 provides a user interface based on the computer keyboard, pointing device and display screen that allows a user to select among different operating modes and graphic display overlay templates used while processing surgical apparatus 18 serial data stream to provide a digital-RGB video image for video overlay console 22. The templates used to produce computer 56 graphic digital-RGB video signal are luminance-keyed. A video overlay circuit sub-system 82 keyer 126 will produce a display at overlaid video signal 128. The information carried by digital-RGB signal 121 is overlaid and totally hides the information carried by video signal 120 in those portions where digital-RGB signal 121 luminance is above a preset luminance key level. All other portions will exclusively show the video contents of video signal 120. Computer 56 digital-RGB video output is delivered as a VGA signal at VGA output port 53 through VGA cable 50 to video overlay console 22 digital-RGB signal input port 78 and from there to video overlay circuit sub-system 82. A scan converter and genlock circuit 122 adjusts the clock rates of video signal 120 and digital-RGB signal 121 and puts them in sync. Luminance keyer 126 receives the digital-RGB genlocked signal. A video mixer 124 finally integrates the synchronized data from the video signal 120, the scan adjusted and genlocked digital-RGB signal 123 and the keyer 126 information to provide an graphic overlaid video signal 128.

Microphone 44 provides an audio signal that corresponds to the plurality of sounds present in the operating room during surgery. These correspond in part to audio signals emitted by a speaker located in surgical apparatus 18 that reflect surgical apparatus events and conditions. Also, the ultrasonic handpiece emits a hissing sound during active phacoemulsification with an intensity that is proportional to ultrasonic power. Microphone 44 allows to pick up these sounds relevant to the surgical case. Audio pre-amplifier 92 provides a properly amplified microphone 44 output signal at audio output port 94. This audio signal may be recorded into the audio track of video-recorder 30 by connecting audio output cable 48 to an audio input of video-recorder 30. Microphone 44 can be multidirectional or unidirectional in a way that some sound sources may be enhanced over others by proper microphone location and orientation.

Signal detector circuit 110 is connected to monitor the data signal 96, video signals 70 and 72 and digital-RGB signal 78 in a non-invasive high impedance manner. Signal status indicator panel 112 provides visual information reflecting the status of each of the signal detector circuit 110 monitored signals. In this way the video overlay console 22 provides information to a user that quickly and easily allows to setup the system and eventually correct operation problems due to missing or improperly connected input signals.

Figure 4:
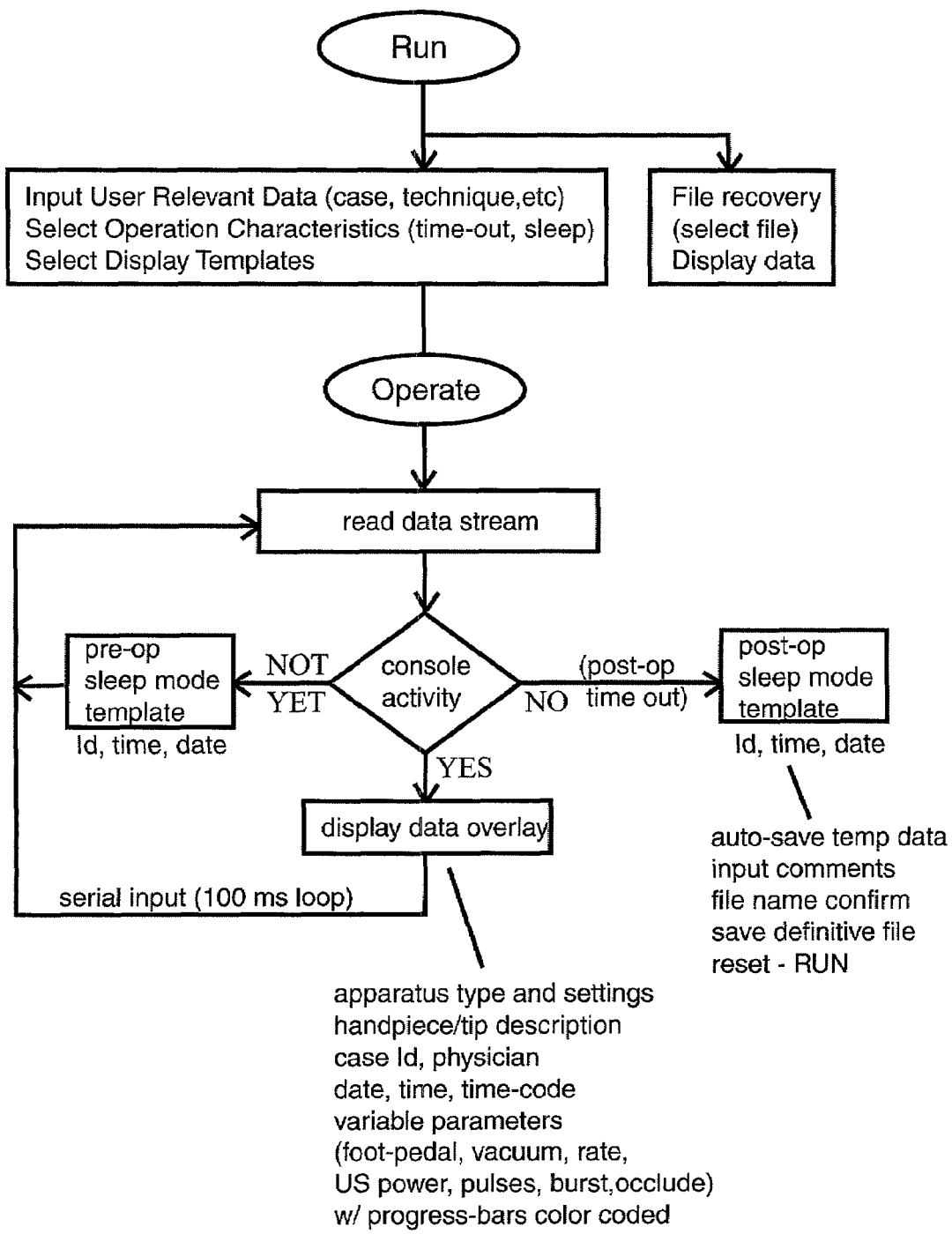
FIG. 4 is a flow chart of the computer program that controls the operation of the video overlay system of the present invention.

FIG. 4. shows a flowchart of the computer program that controls the digital-RGB graphic video image. The program runs on computer 56 and provides a user interface composed of the computer keyboard, pointing device, display screen and input/output device, in a way that it allows a user to introduce alphanumeric data, to select operational modes, to select among different pre-designed graphic display templates, to introduce and select custom made screen templates, to select time-out periods and to change between different templates. It also allows to save and recover data stored during each surgical procedure.

The computer program provides the possibility to use templates that incorporate analog graphic representation of numerical information on the overlay screen to inform a viewer in an intuitive way the magnitude of relevant parameters such as vacuum limit or others type of values that are difficult to perceive in numerical form due to their fast fluctuations. Color changes in the graphic or numerical displays can be programmed to reflect special situations such as over-limit values of relevant data.

The user interface allows user interaction for archiving a time-coded file with the relevant data onto non-volatile digital storage media for subsequent retrieval, analysis. The file data time-code matches the time-code graphic information overlaid onto the video recording of the surgery allowing precise integration between video-recorded surgical events and the archived data.

The user interface also allows a user to retrieve the stored relevant data from a surgical case and analyze several aspects such as maximum values, accumulated ultrasonic energy, rate of change of aspiration line vacuum, etc. The digitally stored data file can be exported to third party computer programs such as spreadsheets and databases for processing.

Using the computer program user interface an operator can instruct the video overlay system 10 to enter into a sleep-mode characterized by a selected overlay screen template or no overlay at all.

Also the video overlay system 10 can be programmed to wake-up on user commands such as depressing a surgical apparatus 18 foot-pedal 17. The system can be preset to enter into sleep-mode after a pre-defined time-out period starting when determined surgical console 18 activities have ended as detected by programmatic analysis of the serial data stream.

The user interface 19 of surgical apparatus 18 can be used as an alternative method to select video overlay console 22 operational modes, by altering in a determined manner the serial data stream through output data port 20 to video overlay system 10.

Description and Operation of Alternative Embodiments

Figure 5:
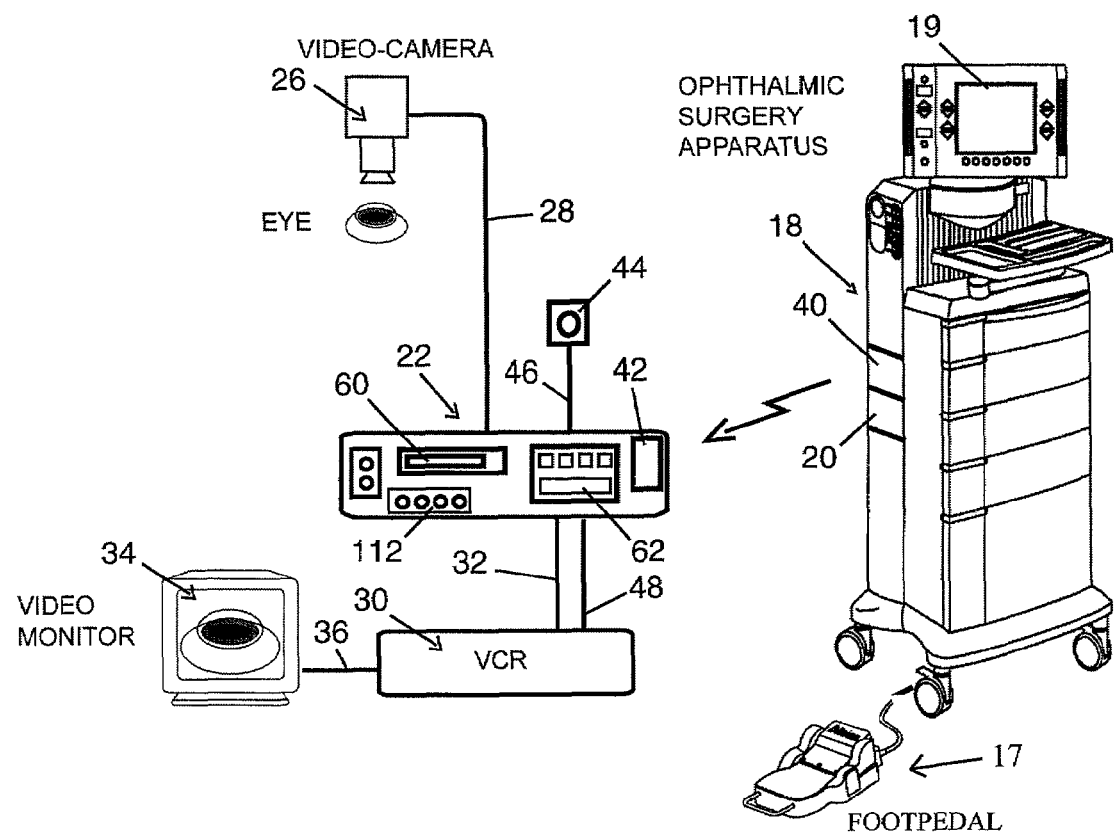
FIG. 5 is a schematic diagram of an alternative embodiment of the video overlay system of the present invention.
Figure 6:
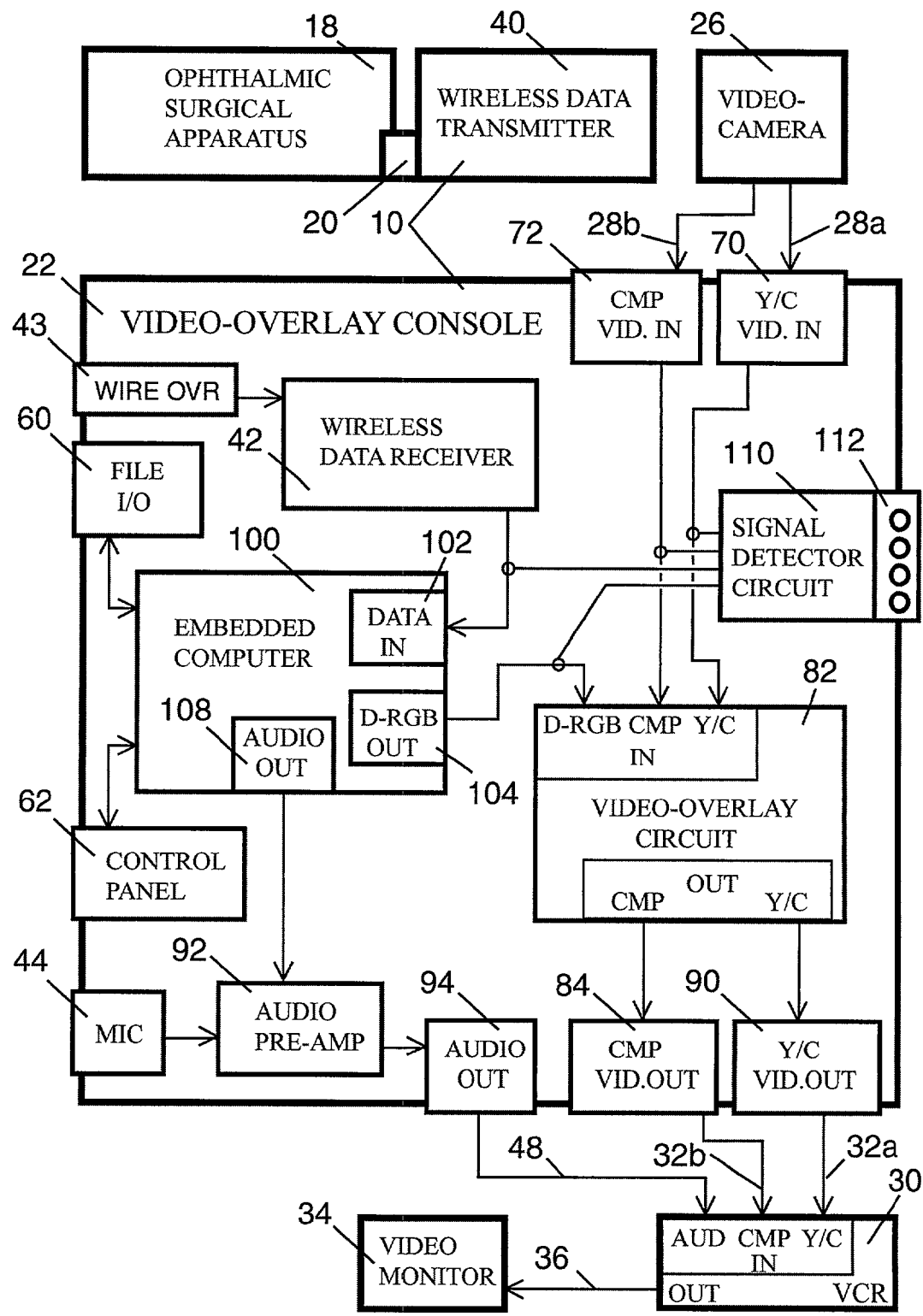
FIG. 6 is a block diagram of an alternative embodiment of the video overlay system of the present invention.

FIG. 5 shows an schematic diagram of an alternative embodiment of the video overlay system of the present invention where video overlay console 22 operates in a stand-alone manner. FIG. 6 depicts a block diagram of this alternative embodiment. On this embodiment computer 56, signal connecting cables 50 and 52 and connector 96 and 58 are replaced by a dedicated embedded computer board 100 integrated into video overlay console 22. Embedded computer 100 serial data port 102 replaces connector 96 and receives the radio-frequency decoded serial data stream from serial data receiver 42. This serial data stream is sent by wireless data transmitter 40 from surgical apparatus 18 serial data port 20 containing the operational parameters of surgical apparatus 18.

An embedded computer 100 digital-RGB video output 104 is connected to the digital-RGB video input of video overlay circuit 82. An embedded computer 100 control panel 62 provides a user interface that can be implemented in several forms. A simple approach is to use push-buttons to select options. An embedded computer file input/output device 60 allows user input in the form of program updates and overlay graphic template loading. Also I/O device 60 allows embedded computer 100 to transfer stored files corresponding to surgical procedures for retrieval, display and analysis in another computer. File input/output device 60 can be implemented using a plurality of devices such as magnetic disk units, optical disk units, non-volatile memory cards, and I/O data ports for connection to another device.

In another aspect, and as an alternative embodiment of the audio capture portion of the present invention, microphone 44 used for surgical room audio pick-up can be complemented or replaced by an audio synthetizer that produces particular sounds related to the surgical apparatus 18 operating status by processing information from the incoming serial data stream, in a similar way as surgical apparatus 18 emits activity related sounds through a loudspeaker. This video overlay 22 audio synthesis function can be implemented by using embedded computer 100 audio hardware and software producing an audio signal at output 108.

Conclusion, Ramifications and Scope

Thus the reader will see that the video overlay system for a surgical apparatus of the invention provides a significant advantage over prior surgical video overlay systems by totally eliminating the dedicated data cable that connects a surgical apparatus with a video overlay console, and replacing it by wireless means of data transmission of the surgical apparatus output data stream. This is a clear advantage over current systems as it eliminates the time consuming need of connecting and disconnecting a cable in a busy operating room.

It also eliminates the risk for persons and property of having another electric cable wondering around in the operating room. This invention allows the video overlay console to remain stationary usually near the video recorder while the surgical apparatus can enter and leave the operating room with the embedded wireless data transmitter module.

Another advantage of the invention is the implementation of a video overlay system equipped with a user interface that allows a user to select among different operating modes and different graphic display overlay templates adding flexibility when compared to current rigid surgical video overlay systems.

Storing the relevant surgical data in a time-coded overlaid video and also in a matching time-coded digital file makes easier to improve surgical technique, to develop research projects related to surgery and to improve surgery teaching.

While the above description contains many specificities these should not be construed as limitations on the scope of the invention, but rather as an exemplification of two preferred embodiments thereof. Many other variations are possible. For example the radio-frequency data transceiver modules can be replaced by other radio-frequency receivers and transmitters using different data rates, frequencies, etc. The wireless nature of the data link also includes any other form of wireless transmission such as infrared light modulation. In this sense, the use of radio-frequency modulation of the power line of the surgical apparatus to send the data stream should be considered within the scope of the present invention. Although not a being an strictly "wireless" technique, the main objective of canceling a dedicated data cable equally achieved.

The video overlay console connection can be performed to different computers. It can be a portable personal computer such as a notebook computer or a stationary personal computer. In the latter case the video overlay console can be enclosed within the stationary computer case providing the appropriate connectors. The wireless data transmitter can be located external to or internal within the surgical apparatus.

Current video standards such as NTSC and PAL can change in the future. Replacement of the video overlay circuit to conform to the new video standards being analog or digital in nature should fall within the scope of the present invention. The type of surgical apparatus and the techniques used to perform a determined surgical procedure that uses the video overlay system can evolve with time into other apparatus and techniques. In this case the relevant parameters could differ significantly from the ones considered today and a re-definition of the valuable parameters should be within the scope of the current invention.

Next generation surgical apparatus and computers can use data protocols that depart from the currently used RS-232, such as USB, FireWire and others. Hardware and software modifications could be necessary to accommodate these new standards without departing from the scope of the present invention. The serial data link 52 between the video overlay console 22 and the computer 56 can use alternative wired or wireless means for data communication. The video signal traveling from the video-camera to the video overlay console and from the video overlay console to the video recorder can use wireless video signal transmission technologies without departing from the present invention.

Accordingly, the scope of the invention should be determined not by the embodiments illustrated but by the appended claims and their legal equivalents.

The invention claimed is:

1. A wireless video overlay system for a surgical apparatus comprising:
   (a) a wireless data transmitter for periodically transmitting a data signal from said surgical apparatus to a video overlay console,
   (b) said video overlay console having a matching wireless data receiver for receiving said surgical apparatus data signal transmitted by said wireless data transmitter
   (c) a computer for processing said surgical apparatus data signal received by said video overlay console into a digital video signal
   (d) a video input within said video overlay console for receiving a surgical field video signal captured with a video-camera
   (e) a digital video input within said video overlay console for receiving said computer generated digital video signal
   (f) a video overlay circuit within said video overlay console for creating an output video signal composed by a combination of said surgical field video signal and said digital video signal in a distribution pattern determined by a key extracted from said digital video signal
   whereby the data used to create said digital video signal by said computer is transmitted from said surgical apparatus to said video overlay console by wireless means.

2. The video overlay system of claim 1 wherein said surgical apparatus is used for ophthalmic surgery.

3. The video overlay system of claim 1 wherein said computer is a personal computer.

4. The video overlay system of claim 1 wherein said computer is an embedded computer enclosed within said video overlay console.

5. The video overlay system of claim 1 further including a signal detector circuit that informs a user about the correct status of the required input signals.

6. The video overlay system of claim 1 further including an audio pre-amplifier to produce a recordable audio output signal from the sounds captured by a microphone.

7. The video overlay system of claim 1 further including an audio synthetizer to produce an audio signal determined by the analysis of said surgical apparatus data signal.

8. The video overlay system of claim 1 further including a control panel for user selection of video overlay console operation mode.

9. The video overlay system of claim 1 further including a control panel for user selection of video overlay graphic templates.

10. The video overlay system of claim 1 further including data storing means to accumulate said input data signals together with a time code.

11. The video overlay system of claim 1 further including data input/output means to export data stored during operation and to load graphic overlay templates.

12. The output video signal of claim 1 further including a graphic representation of a time code.

13. The output video signal of claim 1 further including a graphic representation of predetermined information selected by a user.

14. A method for obtaining a user configurable surgical video overlay output signal by overlaying a graphic representation of output data signals produced by a surgical apparatus onto a surgical field video signal comprising:
   (a) receiving said data signal from said surgical apparatus
   (b) receiving said surgical field video signal from a video-camera to be used as a background image to obtain said video overlay output signal
   (c) converting said data signal into a graphic representation digital video signal of the data contained in said data signal in a data storage means for said computer means, using a computer means,
   (d) storing said data signal in a data storage means for said computer means,
   (e) providing a computer program for said computer means the computer means executes the steps of:
      (1) detects and decodes each parameter contained in said data signal
      (2) produces a video graphic representation based on said data signal parameters and on a predetermined graphic template selected by a human operator.
      (3) changes between predetermined graphic templates according to a predetermined operation mode selected by a human operator
      (4) stores in said non-volatile data storage means the parameters decoded from said data signal together with a time code
   (f) providing user interface means for a human operator to select from a plurality of options regarding different operation modes that change the graphic representation pattern used to produce said overlay output signal as determined by said computer program according to predetermined conditions
   (g) providing user interface means for a human operator to select from a plurality of options regarding different graphic representation video signal templates as determined by said computer program
   (h) providing a video overlay circuit to produce said surgical video overlay output signal by overlaying said digital video signal onto said surgical field video signal
   whereby said video overlay circuit produces a video overlay output signal containing a graphic representation of the surgical parameters in a predetermined pattern selected by a human operator through said user interface whereby said computer program changes the graphic representation pattern used to produce said overlay output signal according to preferred operation modes as selected by a human operator through said user interface.

15. The method of claim 14 wherein said surgical apparatus is used for ophthalmic surgery.

16. The method of claim 14 further providing a signal detector circuit to inform a user about the correct status of the required input signals.

17. The method of claim 14 further providing an audio pre-amplifier to produce a recordable audio output signal from the sounds captured by a microphone.

* * * * *